US005468227A

United States Patent [19]

Haskell

[11] Patent Number: 5,468,227

[45] Date of Patent: Nov. 21, 1995

[54] POULTRY VACCINATOR

[76] Inventor: Ora Haskell, 199 Prospect Hill Rd., Colchester, Conn. 06415

[21] Appl. No.: 222,223

[22] Filed: Apr. 4, 1994

[51] Int. Cl.$^6$ .............................. A61M 5/20; A61D 7/00

[52] U.S. Cl. .......................... 604/156; 119/713; 604/131

[58] Field of Search .................................. 604/131, 134, 604/135, 137, 144, 156, 157; 119/713

[56] References Cited

U.S. PATENT DOCUMENTS

| | | | |
|---|---|---|---|
| 2,319,938 | 5/1943 | Markins | 119/97 |
| 2,847,993 | 8/1958 | Woodruff | 128/191 |
| 2,984,240 | 5/1961 | Eames | 128/185 |
| 3,880,122 | 4/1975 | Randolph et al. | 119/97 R |
| 3,964,481 | 6/1976 | Gourlandt et al. | 604/156 |
| 4,108,176 | 8/1978 | Walden | 604/144 |
| 4,276,879 | 7/1981 | Yiournas | 604/156 |
| 4,316,464 | 2/1982 | Peterson | 128/253 |
| 4,449,968 | 5/1984 | Peterson | 604/24 |
| 4,643,354 | 2/1987 | Stowe | 239/1 |
| 4,758,227 | 7/1988 | Lancaster et al. | 604/156 |
| 4,863,443 | 9/1989 | Hornung | 604/156 |
| 5,199,952 | 4/1993 | Marshall et al. | 604/156 |
| 5,306,251 | 4/1994 | Alexander | 604/137 |
| 5,312,353 | 5/1994 | Boggess et al. | 604/156 |

*Primary Examiner*—Paul J. Hirsch
*Attorney, Agent, or Firm*—Ira S. Dorman

[57] ABSTRACT

Poultry inoculation apparatus includes a solenoid-driven hypodermic needle which pierces the web of the constrained wing of a bird. A positive displacement pump delivers vaccine or other treating liquid to the needle for administration while the needle is in extended position.

5 Claims, 5 Drawing Sheets

POULTRY VACCINATOR

BACKGROUND OF THE INVENTION

Vaccination of chickens and other fowl that are sold for human consumption is customarily done for protection against various diseases. Although so-called "automatic syringes" are available, in many instances inoculation is done manually. In any event, the techniques presently employed suffer from a number of disadvantages, including the likelihood of operator injury, inadequate asepsis, a tendency for misadministration (due especially to inadequate immobilization of the bird), inordinate manpower requirements, and difficult and unreliable delivery of the substance for injection.

The prior art does not appear to have adequately addressed these problems. Markins U.S. Pat. No. 2,319,938 describes a device for restraining poultry while blood tests are being made or where vaccinations are to be given, but provides no associated means for effecting delivery and administration of vaccine. Peterson U.S. Pat. No. 4,316,464 describes a poultry vaccination system, wherein vaccine is sprayed upon chicks confined within a chamber.

Accordingly, it is the primary object of the present invention to provide apparatus for administrating a substance to poultry and the like, which apparatus is safe and facile to use, affords improved asepsis, and is rapid, efficient, reliable, and economical in operation.

It has now been found that the foregoing and related objects of the invention are readily attained by the provision of inoculating apparatus comprising structure providing an injection location; a substance-delivery system, including a delivery device and supply means operatively connected to the delivery device; and means for mounting the delivery device for movement between a delivery position, adjacent the injection location, and a position displaced therefrom. The apparatus also includes drive means that is capable of actuation for effecting movement of the delivery device from its displaced position to its delivery position, and means for selectively actuating the drive means for effecting such movement of the delivery device. Means is also provided for supporting a bird adjacent the injection location, and for engaging a wing of the supported bird for positioning the wing at the injection location.

The support means will desirably comprise a trough into which the bird may be placed, with the wing-positioning means defining a recess into which the bird's wing may be extended. The mounting means will usually mount the delivery device for reciprocal movement, the drive means will normally comprise an electric solenoid, the actuating means will advantageously comprise a switch disposed near the injection location, and the delivery device will normally include a hypodermic needle. In such latter case, the substance-supply means will most desirably comprise a liquid reservoir and the delivery system will include a pump that is operatively connected for effecting delivery of a liquid substance from the reservoir to the needle.

DETAILED DESCRIPTION OF THE ILLUSTRATED EMBODIMENT

Figure 1:
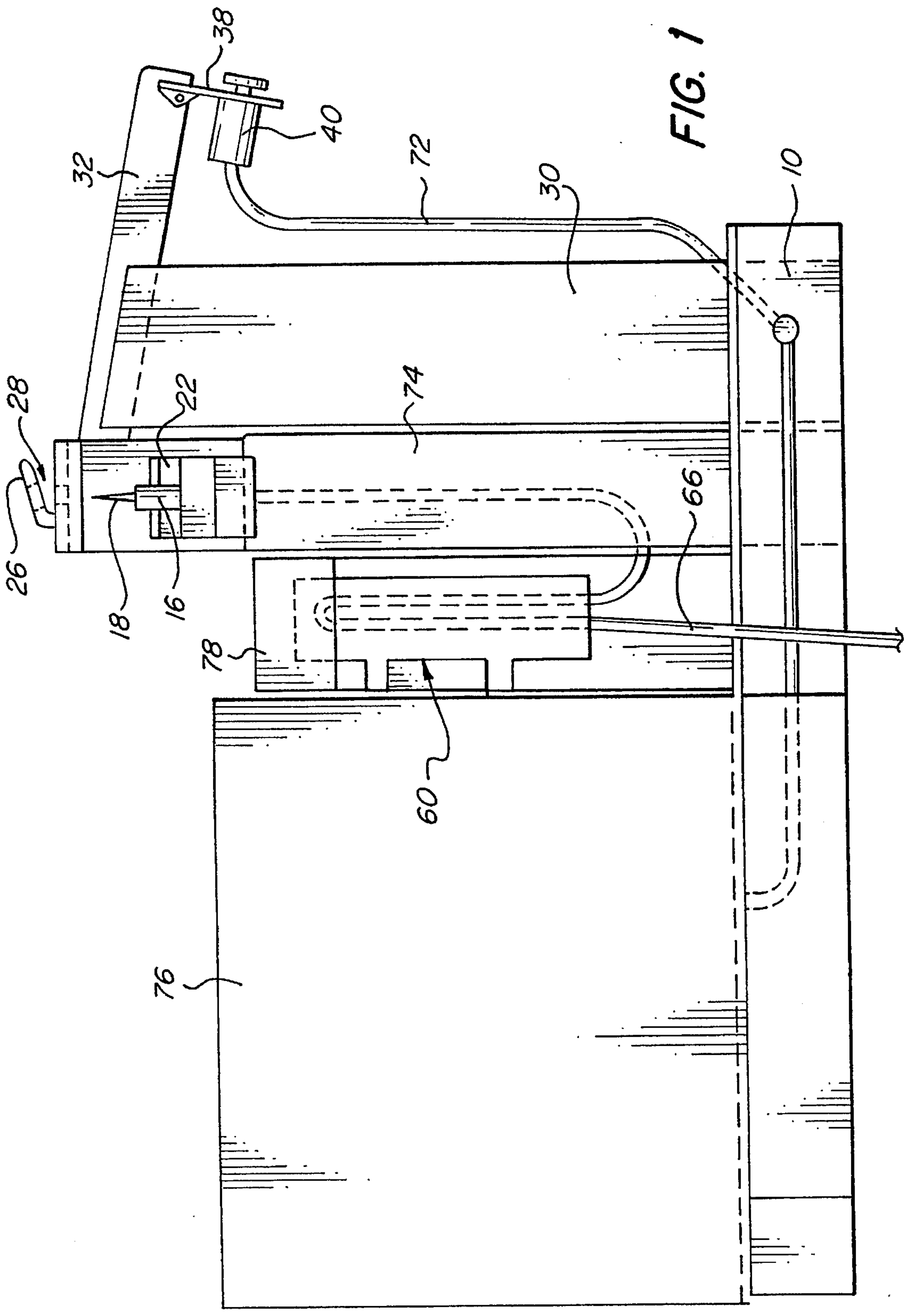
FIG. 1 is a side elevational view of apparatus embodying the present invention.
Figure 2:
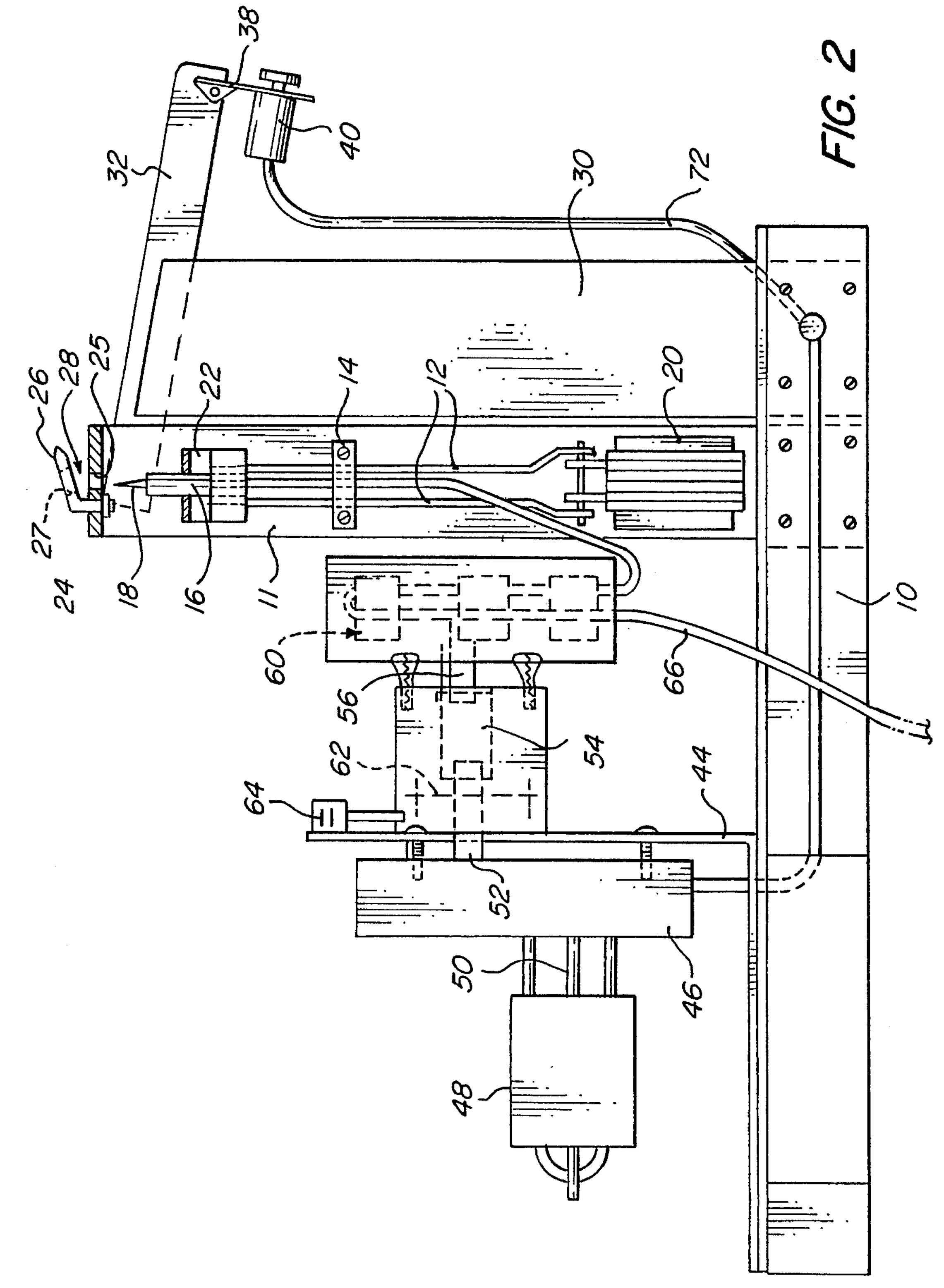
FIG. 2 is a view similar to FIG. 1, showing the apparatus with enclosures and covering panels removed.
Figure 3:
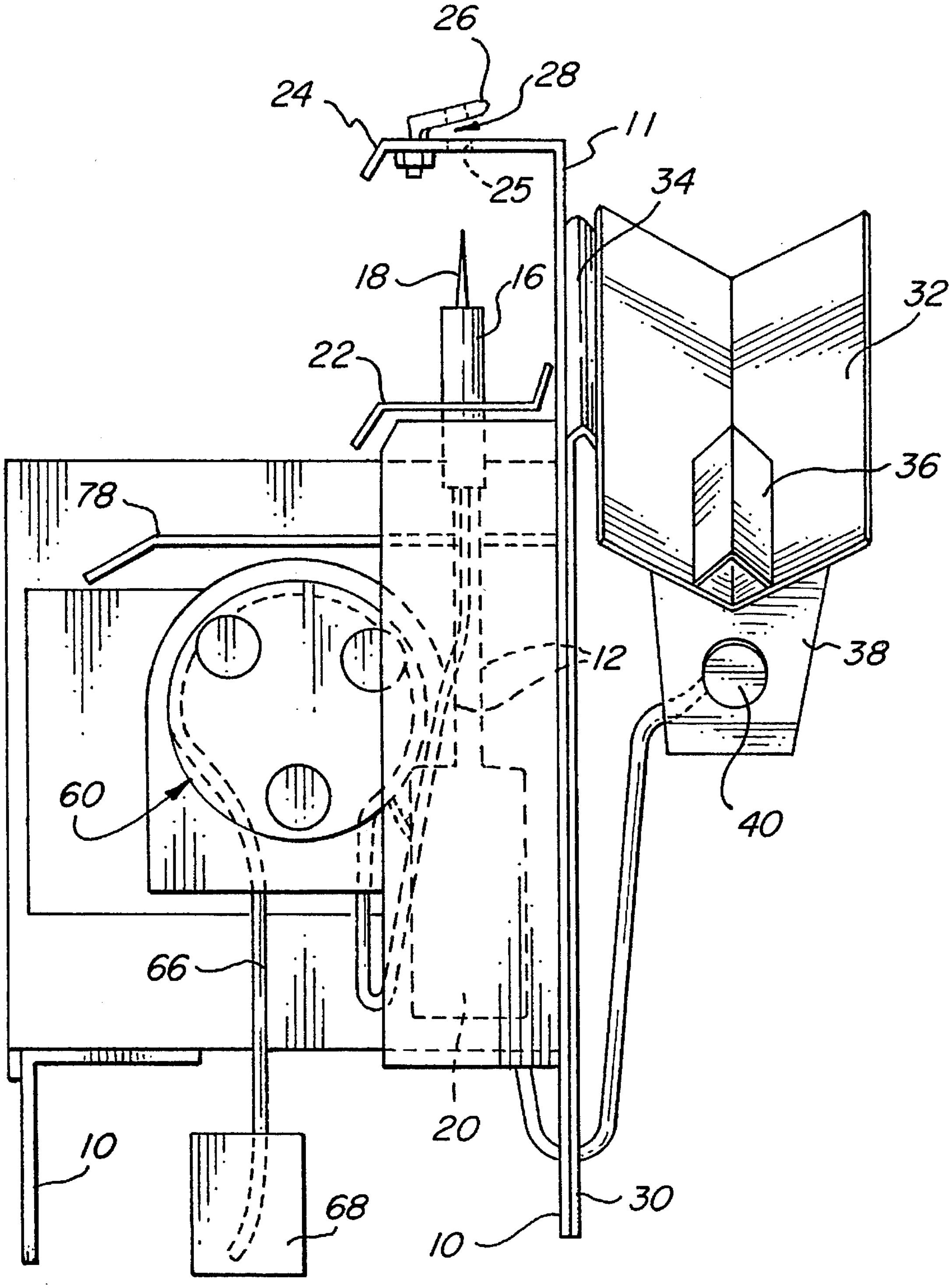
FIG. 3 is a front elevational view of the apparatus (i.e., taken from the operator's position)
Figure 4:
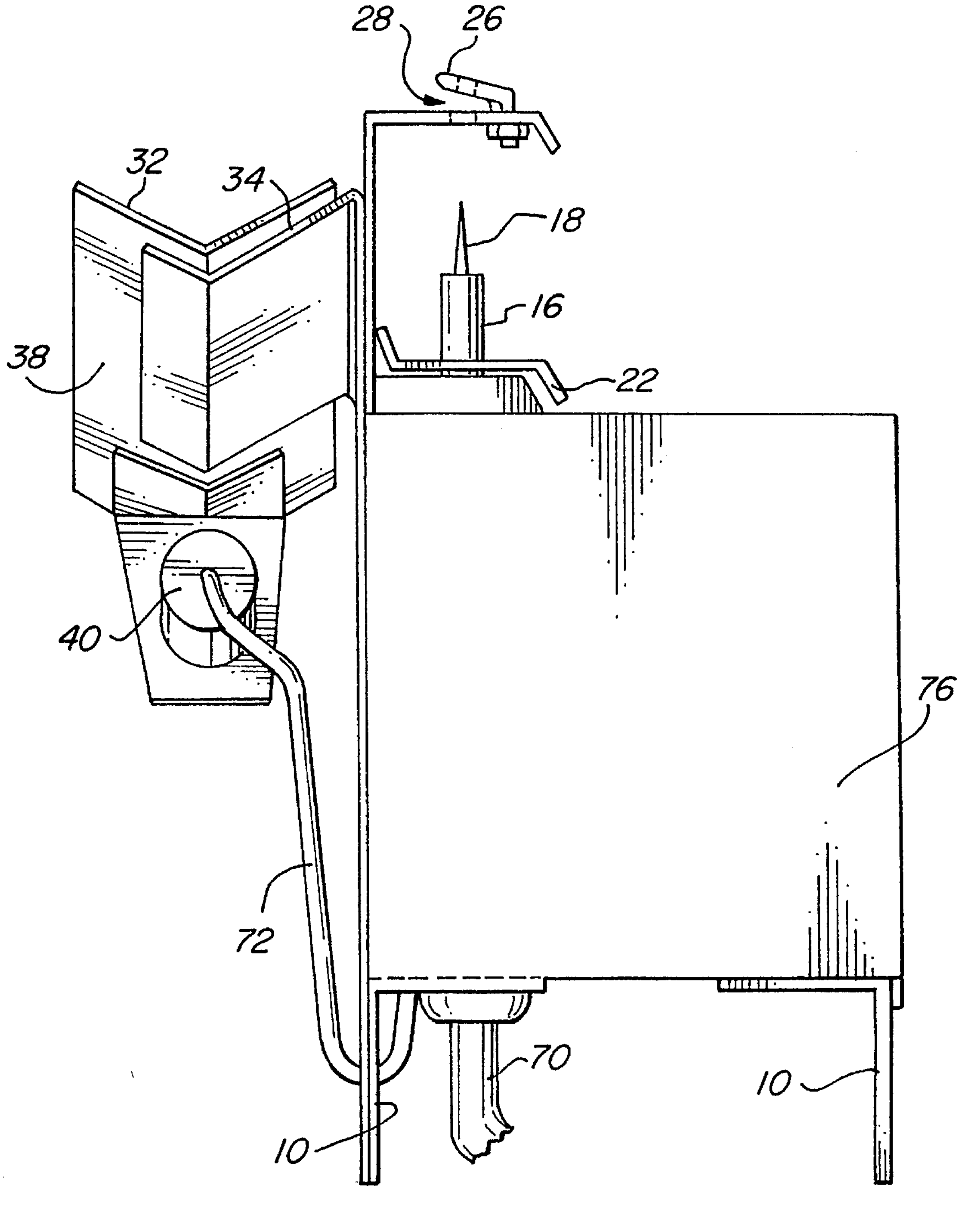
FIG. 4 is rear elevational view thereof.
Figure 5:
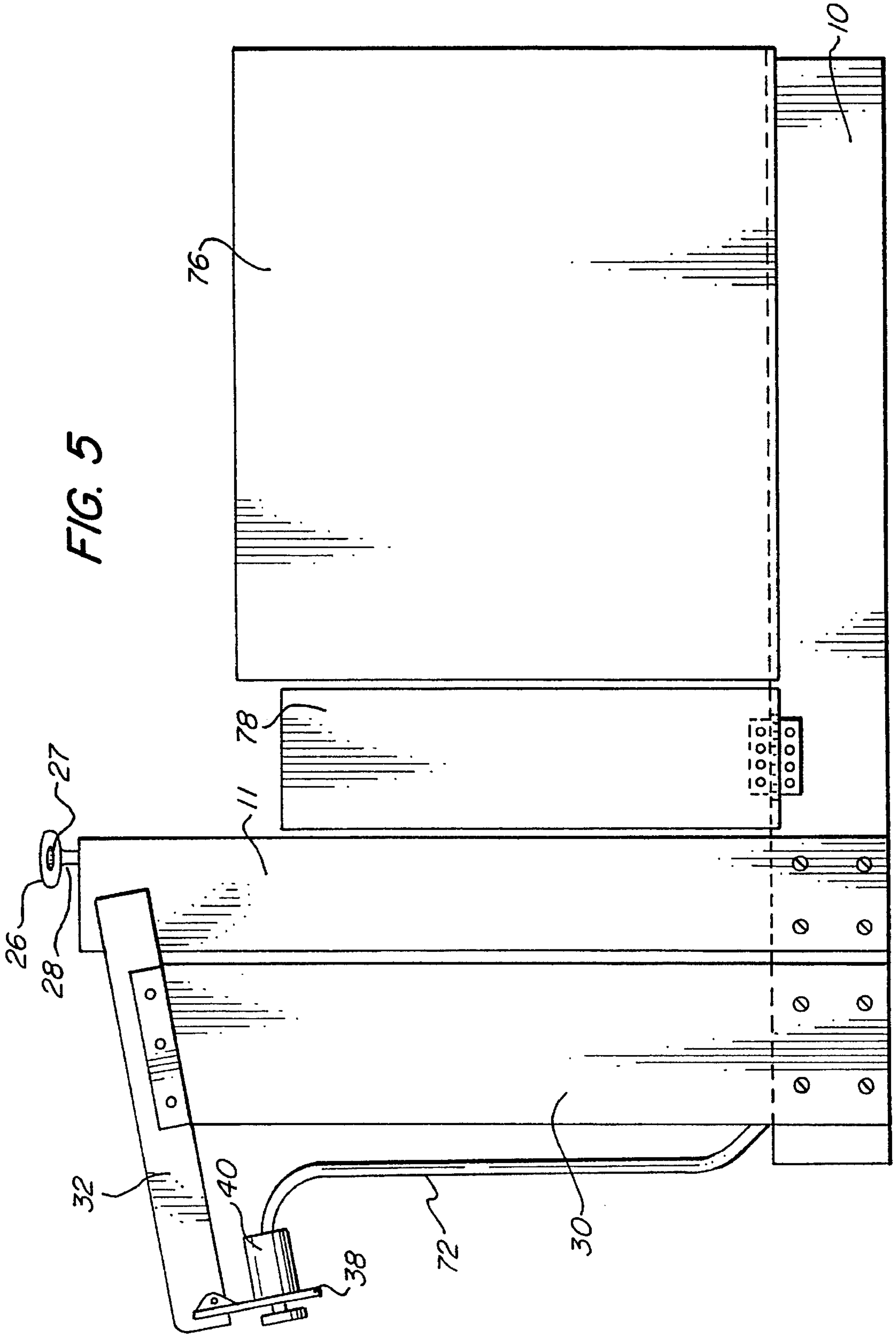
FIG. 5 is an elevational view taken from the side opposite to that of FIGS. 1 and 2.

Turning now in detail to the appended drawings, therein illustrated is apparatus embodying the present invention, the components of which are supported upon a pair parallel, right-angle beams or base rails 10. An upstanding mounting bar 11 is attached at its lower end to one of the beams 10 and serves to slidably support a pair of actuating arms 12, the latter being held in place against the bar 11 by a retaining strip 14. A needle holder 16 is attached to the upper ends of the arms 12, and it in turn supports a hypodermic needle 18; a drip shield 22 is affixed at the base of the holder 16. The opposite ends of the arms 12 are attached to an electric solenoid 20, actuation of which drives the needle 18 upwardly through the right-angle plate 24 disposed at the top of the bar 11, the plate 24 having an aperture 25 therein to permit the needle 18 to pass therethrough. A hold-down loop 26 is fastened to plate 24 and is spaced therefrom to define a recess 28; it too has an aperture 27 for passage of the needle 18.

A second mounting bar 30 is similarly attached at its lower end to the same base rail 10, and supports a V-shaped trough 32 at its upper end, a suitable bracket 34 being provided for that purpose. A leg separator 36 is provided at the forward end of the trough 32, and a depending mounting plate 38 supports a push-button switch 40.

A large right-angle bracket 44 is supported between the rails 10 at a rearward location. The upright panel of the bracket 44 mounts a transmission unit 46 and an electric motor 48; power is transmitted from the motor shaft 50 to the shaft 52, which in turn carries a coupling 54 connected to the drive shaft 56 of a positive-displacement roller pump, generally designated by the numeral 60. Pinwheel control plate 62 is affixed to the shaft 52 for rotation therewith, and serves to actuate a microswitch 64 for controlling power to the motor 48 and solenoid 20. A resiliently compressible tube 66 circumscribes the roller array of pump 60 and is connected at its discharge end to the needle holder 60, the intake end being immersed in the liquid substance that is to be administered, which is contained in a reservoir 68. Power is supplied to the apparatus through an electric cable contained in duct 70, which is connected by way of wire 72 and switch 40 to the motor 48 and solenoid 20. Enclosures 74, 76 and 78 normally cover the solenoid assembly, the motor components, and the pump components, respectively.

In use, the operator places the bird into the trough 32, grasping both of its legs with one hand; the push button of the switch 40 is so positioned that it can be reached by the same hand. With his other hand, the operator then extends the wing into the recess 28 defined by the hold-down loop 26, thereby positioning the wing web over the aperture 25 and needle 18. The injection cycle is initiated by depression of the push button, concurrently energizing the motor 48 and the solenoid 20. As the needle 18 is driven through the wing web, therefore, vaccine is pumped from the reservoir 68 to the needle, discharging therefrom into the wound produced. Actuation of the microswitch 64 by contact with a pin of the pinwheel 62 breaks the circuit, thereby terminating flow and effecting retraction of the needle.

As will be appreciated, the apparatus described promotes operator safety and proper administration of vaccine by fixing the location of the hypodermic needle, and also by facilitating immobilization of the bird. The latter results from the physical constraints provided by the trough and the hold-down loop, as well as from impalement of the bird's wing on the needle. Minimized risk of injury and manpower savings are both afforded by the one-person operation of the apparatus, and asepsis is promoted by use of a sealed reservoir, from which delivery occurs directly to the needle through a closed system. The avoidance of valves and other moving parts helps to ensure trouble-free operation, and the semi-automatic nature of the apparatus, coupled with the other features described, enables rapid and efficient operation. Thus, it can be seen that the present invention provides inoculating apparatus that is safe and facile to use, that affords improved asepsis, and that is fast, efficient, reliable, and economical in operation.

Having thus described the invention, what is claimed is:

1. Apparatus for inoculating poultry and the like, comprising: structure providing an injection location; a substance-delivery system, including a delivery device and supply means operatively connected to said delivery device; mounting means for mounting said delivery device for movement between a delivery position adjacent said injection location and a position displaced therefrom; drive means capable of actuation for effecting movement of said delivery device from said displaced position to said delivery position; actuating means for selectively actuating said drive means for effecting movement of said delivery device to said delivery position; and first and second position-controlling means, said first position-controlling means constituting support means adjacent said injection location for providing stationary underlying support for the body of a bird to be inoculated while permitting lateral extension of at least one wing, and said second position-controlling means constituting wing-positioning means for engaging a wing of a bird so supported by said support means, and for positioning the wing at said injection location, said injection location being spaced laterally from said support means and requiring extension of the wing of the bird from its body so as to permit engagement of the wing by said wing-positioning means.

2. The apparatus of claim 1 wherein said support means comprises a trough into which the bird to be inoculated can be placed, and wherein said wing-positioning means defines a recess into which the bird's wing can be extended.

3. The apparatus of claim 1 wherein said actuating means comprises a switch operatively disposed near said injection location.

4. The apparatus of claim 1 wherein said mounting means mounts said delivery device for reciprocal movement, and wherein said drive means comprises a solenoid.

5. The apparatus of claim 1 wherein said delivery device comprises a hypodermic needle and said supply means comprises a liquid reservoir, and wherein said substance-delivery system further includes a pump operatively connected for effecting delivery of a liquid substance from said reservoir to said needle.

* * * * *